United States Patent [19]

Parsons et al.

[11] Patent Number: 4,634,716
[45] Date of Patent: Jan. 6, 1987

[54] SUBSTITUTED N-CARBOXYMETHYL-AMINOACYLAMINOALKANOIC ACIDS USEFUL AS ANTIHYPERTENSIVE AGENTS

[75] Inventors: William H. Parsons, Rahway; David Taub, Metuchen, both of N.J.

[73] Assignee: Merck & Co., Inc., Rahway, N.J.

[21] Appl. No.: 492,991

[22] Filed: May 16, 1983

Related U.S. Application Data

[63] Continuation-in-part of Ser. No. 430,916, Sep. 30, 1982, abandoned.

[51] Int. Cl.$^4$ ............... C07D 207/09; C07D 401/04; C07D 401/12; C07D 405/04; C07D 417/12; C07D 417/04; C07D 409/12; C07D 409/04; A61K 31/44; A61K 31/47; A61K 31/425; A61K 31/40

[52] U.S. Cl. .................. 514/423; 546/273; 514/11; 546/274; 546/122; 514/19; 546/140; 546/147; 514/300; 546/174; 546/175; 514/307; 548/156; 548/159; 514/308; 548/180; 548/181; 514/314; 548/204; 548/207; 514/333; 548/214; 548/327; 514/336; 548/328; 548/336; 514/337; 548/454; 548/455; 514/338; 548/467; 548/468; 514/339; 548/494; 548/510; 514/340; 548/517; 548/518; 514/341; 548/525; 548/527; 514/342; 548/540; 260/998.2; 514/367; 514/365; 514/372; 514/373; 514/394; 514/397; 514/419; 514/415; 514/422; 546/256; 546/281; 546/280; 546/278; 546/268; 546/269; 546/270; 546/271; 546/272

[58] Field of Search ............... 548/540; 260/112.5 R, 260/998.2; 514/11, 19, 300, 307, 308, 314, 333, 336, 337, 338, 339, 340, 341, 342, 367, 365, 372, 373, 394, 397, 419, 415, 422, 423; 546/256, 281, 280, 278

[56] References Cited

U.S. PATENT DOCUMENTS 4,113,715  9/1978  Ondetti et al. ............... 260/112.5 R
4,129,571  12/1978  Ondetti et al. ............... 260/326.2
4,154,960  5/1979  Ondetti et al. ............... 562/426
4,374,829  2/1983  Harris et al. ............... 260/112.5 R

FOREIGN PATENT DOCUMENTS 50800  5/1982  European Pat. Off. ..... 260/112.5 R
54862  6/1982  European Pat. Off. ......... 260/112.5
2704985  8/1977  Fed. Rep. of Germany.
2720996  10/1978  Fed. Rep. of Germany.
2810261  9/1979  Fed. Rep. of Germany.
3046271  8/1981  Fed. Rep. of Germany.

OTHER PUBLICATIONS

Abstract of ACS Meeting of 9-11-78 entitled "Superactive Analogs of the Angiotensin Converting Enzyme Inhibitor BPP$_{9a}$ Containing L-3,4-Dehydroproline".
Patchett et al., in "A New Class of Angiotensin-Converting Enzyme Inhibitors", *Nature*, vol. 228, No. 5788, pp. 280–283 (Nov. 20, 1980).

Primary Examiner—John M. Ford
Attorney, Agent, or Firm—Salvatore C. Mitri; Michael C. Sudol

[57] ABSTRACT

Compounds of the formula:

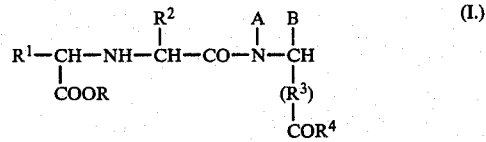

where R$^3$ is

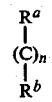

where n is 1–3 and the R$^a$'s and R$^b$'s are independently hydrogen or loweralkyl; and pharmaceutically acceptable salts thereof; are inhibitors or angiotensin I converting enzyme useful as antihypertensive agents.

7 Claims, No Drawings

SUBSTITUTED N-CARBOXYMETHYL-AMINOACYLAMINOALKANOIC ACIDS USEFUL AS ANTIHYPERTENSIVE AGENTS

This application is a continuation-in-part of application Ser. No. 430,916 filed Sept. 30, 1982, now abandoned.

BACKGROUND OF THE INVENTION

1. Field of the Invention

The present invention is concerned with novel substituted N-carboxymethyl-aminoacylaminoalkanoic acid compounds which are effective inhibitors of angiotensin I converting enzyme. These novel compounds are, consequently, combined with pharmaceutically acceptable carriers to form pharmaceutical compositions of the present invention are are used in a method of treating hypertension.

Angiotensin II, a powerful vasoconstrictor hormonal peptide, is formed from the inactive angiotensin I by the action of angiotensin-converting enzyme. Recently, potent inhibitors of angiotensin-converting enzyme have been reported which are capable of lowering the blood pressure in hypertensive patients. The novel substituted N-carboxymethyl-aminoacylaminoalkanoic acid compounds of the present invention are also potent inhibitors of angiotensin-converting enzyme.

2. Brief Description of the Prior Art

U.S. Pat. Nos. 4,113,715; 4,129,571; and 4,154,960 disclose substituted acyl derivatives of amino acids which are useful as angiotension converting enzyme inhibitors. More specifically, these compounds are mercapto substituted acyl amino acids and derivatives thereof including the clinically effective antihypertensive compound, captopril, i.e., D-3-mercapto-2-methylpro-panoyl-L-proline.

The foregoing prior art compounds are not dipeptide derivatives as are the compounds of the present invention. Furthermore, these prior art compounds contain an essential sulfhydryl substituent or derivative thereof whereas those of the present invention do not. In addition, the dipeptide compounds of the present invention are unusual dipeptides whose N-terminus bears a carboxymethyl group which is preferably further substituted on the methyl group. In addition, the carboxyl group(s) may also be converted to ester, amide and salt derivatives. In effect, the compounds of the present invention are hybrids formed by fusing α-amino acids onto dipeptides by means of a nitrogen shared by these two part-structures. This structural arrangement is rare in the field of synthetic and natural peptides and is not suggested or disclosed by the mercaptoacyl type functions of the two prior art patents identified above.

German Patent Application Nos. 2704-985 and 2720-996 describe hypotensive carboxy-actyl-proline derivatives and (N)-carboxyalkanoyl amino acid derivatives; and German Patent Application No. 2810-261 describes thio-substituted (N)-propionylamino acid derivatives which are hypotensive angiotensin converting enzyme inhibitors.

However, none of these references show or suggest any of the compounds of the present invention, which contain the $R^3$ functionality described herein.

An abstract of ACS meeting of 9-11-78 entitled "Superactive Analogs of the Angiotensin Converting Enzyme Inhibitor BPP$_{9a}$ Containing L-3,4-Dehydroproline" describes the use of dehydroproline on various peptides, none of which, however, are similar to the compounds of the present invention.

German Pat. No. 30 46 271 A1 discloses optically active N-mercaptoalkanoylaminoacids which are useful as angiotensin converting enzyme inhibitors. Although this reference teaches that the claimed compounds have the same utility as those of the present invention, the compounds disclosed in the reference differ materially and significantly from those of the present invention especially since all of the reference compounds are mercapto-based.

Patchett et al., in "A New Class of Angiotensin-converting Enzyme Inhibitors", Nature, Vol. 288, No. 5788, pp. 280–283 (Nov. 20, 1980), describe certain N-carboxymethyldipeptides. However, the substituted N-carboxymethyl-(amino acid)pyrrolidinealkanoic acid compounds of the present invention are readily distinguishable by the presence of the $R^3$ functionality described herein.

DETAILED DESCRIPTION OF THE INVENTION AND PREFERRED EMBODIMENTS

In its broadest aspect, the present invention relates to novel substituted N-carboxymethyl-aminoacylaminoalkanoic acid compounds of the formula:

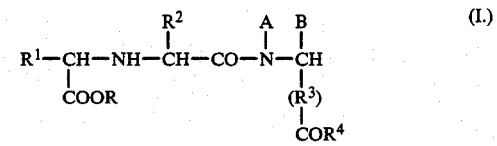

wherein:

R is hydrogen; loweralkyl; aralkyl; aryl; or mono- or di-substituted aryl wherein the substituents are chloro;

$R^1$ is hydrogen; alkyl of from 1 to 12 carbon atoms which include branched, cyclic and unsaturated alkyl groups; substituted loweralkyl wherein the substituent can be halo, hydroxy, carboxy, carboxamido, loweralkylthio, loweralkoxy, loweralkoxycarbonyl, loweraralkoxycarbonyl, amino, loweralkylamino, lowerdialkylamino, acylamino; substituted loweralkylamino wherein the substituent can be halo, hydroxy, alkoxy or cyano; arloweralkylamino; cyclic amino; oxo, thio or ureido; aryloxy; arylthio; aralkyloxy; aralkylthio; benzofused cycloalkyl or bicycloalkyl of from 8–12 carbon atoms; aryl or heteroaryl which may be mono-, di- or trisubstituted by loweralkyl, hydroxy, loweralkoxy, halo, amino, acylamino, loweralkylthio or aminoloweralkyl; benzofused cycloalkyl or bicycloalkyl of from 8 to 12 carbon atoms; arloweralkyl; arloweralkenyl; heteroloweralkyl and heteroloweralkenyl in which the aryl or heteroaryl rings may be mono-, di- or tri-substituted by halo, loweralkyl, hydroxy, loweralkoxy, amino, loweralkylamino, diloweralkylamino, aminoloweralkyl, acylamino, carboxy, haloloweralkyl, nitro, cyano or sulfonamido; aralkyl or heteroaralkyl which include branched loweralkyl groups; substituted aralkyl or substituted heteroaralkyl which include branched loweralkyl groups wherein the loweralkyl groups can be substituted by amino, acylamino, or hydroxyl and the aryl and heteroaryl groups can be substituted by halo, dihalo, loweralkyl, hydroxy, loweralkoxy, aryloxy, aroyl, arylthio, amino, aminoloweralkyl, loweralkanoylamino, aroylamino, lowerdialkylamino, loweralkylamino, hydroxy, hydroxyloweralkyl, trihaloloweralkyl, nitro, cyano, or sulfonamido; any of the arloweralkyl or alkenyl and heteroloweralkyl or alkenyl groups described above in which the aryl or heteroaryl ring is partially or completely hydrogenated; substituted loweralkyl having the formula $R_A{}^1(CH_2)_n-Q-(CH_2)_m$ wherein n is 0-2, m is 1-3, $R_A{}^1$ is aryl or heteroaryl optionally substituted by amino, lowerdialkylamino, loweralkylamino, hydroxy, hydroxyloweralkyl, aminoloweralkyl, trihaloloweralkyl, cyano, nitro, sulfonamido, aroyl, loweralkyl, halo, dihalo, and loweralkoxy, and Q is O, S, SO, $SO_2$, $N-R_B{}^1$, $CONR_C{}^1$, $NR_C{}^1CO$, CH=CH wherein $R_B{}^1$ is hydrogen, loweralkyl, aryl, aralkyl, loweralkanoyl, or aroyl, and $R_C{}^1$ is hydrogen, or loweralkyl;

$R^2$ is hydrogen; loweralkyl; hydroxyloweralkyl; acylaminoloweralkyl; aminoloweralkyl; dimethylaminoloweralkyl; haloloweralkyl; guanidinoloweralkyl; aralkyl, heteroaralkyl, substituted aralkyl, or substituted heteroaralkyl, where the alkyl portion is loweralkyl and the substituents are halo, dihalo, loweralkyl, hydroxy, loweralkoxy, aryloxy, aroyl, arylthio, amino, aminoloweralkyl, loweralkanoylamino, aroylamino, lowerdialkylamino, loweralkylamino, hydroxyloweralkyl, trihaloloweralkyl, nitro, cyano, or sulfonamido; mercaptoloweralkyl; or loweralkylthioloweralkyl; in the group:

A is
(a) alkyl, including branched unsaturated and cyclic alkyl of 3 to 8 carbon atoms;
(b) benzofused cycloalkyl or bicycloalkyl of 8 to 12 carbon atoms;
(c) aryl or heteroaryl groups which may be mono-, di- or trisubstituted by loweralkyl; loweralkoxy, halo, amino, acylamino, hydroxy, acyl or acyloxy, and corresponding groups in which the aryl or heteroaryl groups are partially or completely hydrogenated;
(d) loweralkyl including branched and unsaturated groups which may be substituted by aryl or heteroaryl groups and corresponding groups in which the aryl or heteroaryl rings are partially or completely hydrogenated;

B is hydrogen or loweralkyl;
or
A and B may be joined, together with the carbon atoms to which they are attached to form a ring having the formulae:

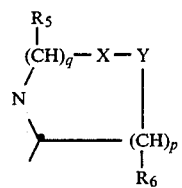

wherein X and Y taken together are

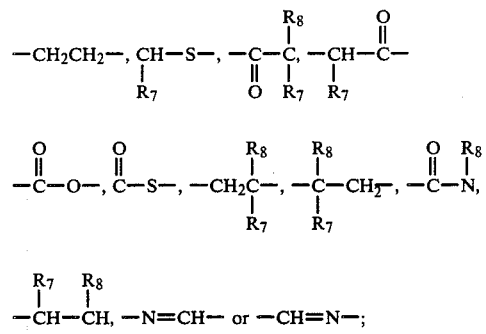

$R_5$ is hydrogen, lower alkyl, aralkyl or aryl;

$R_6$ and $R_7$ individually are hydrogen; loweralkyl; cycloalkyl; aryl; aralkyl; heteroaryl; loweralkyloxy; loweralkylthio; aryloxy; arylthio; arloweralkyloxy; arloweralkylthio; hydroxy; acyloxy; acylloweralkyl; halo; amino; mono- or disubstituted loweralkylamino; arloweralkylamino; heteroloweralkylamino acylamino in which the acyl group may be loweralkanoyl, aroyl, heteroaroyl or heteroloweralkanoyl; carbamoyl or N-substituted carbamoyloxy; including any of these groups containing an aromatic ring wherein said ring may be mono-, di- or trisubstituted by loweralkyl, loweralkoxy, loweralkylthio, halo, hydroxy, aryl, aryloxy, arylthio or aralkyl; any of the groups recited above containing an aryl or heteroaryl group in which these groups are partially or completely hydrogenated;

$R_8$ is hydrogen, loweralkyl, cycloalkyl, aryl, substituted aryl wherein the substituent can be halo, hydroxy, alkoxy, amino, or loweralkyl; or $R_7$ and $R_8$ taken together may be oxo or together with the carbon atoms to which they are attached form a 3 to 6 membered ring which may contain 0, 1 or 2 atoms of N, S or O;

p and q are independently 0 to 3;

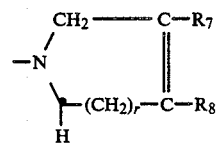

wherein $R_7$ and $R_8$ are as defined above and r is 0, 1 or 2;

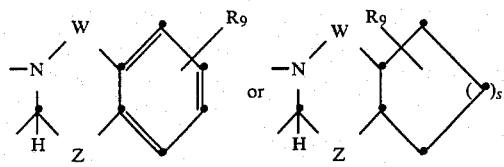
(3)

wherein: W is absent; —CH₂—;

N; or S; Z is —(CH₂)$_t$, wherein t is 0 to 2, provided that t may not be O when W is absent; —O—; —N—, or —S—;

R₉ is hydrogen; loweralkyl; loweralkoxy; hydroxy; halo; loweralkylthio; amino; acylamino; or cyano; s is 1 to 3;

(4) a bicyclic derivative of a 5 or 6 membered N-heterocycle having the formula

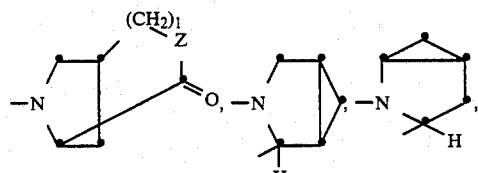

where
l = 0 or 1, and
Z = O or NH

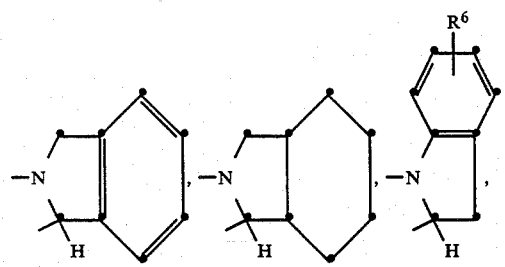

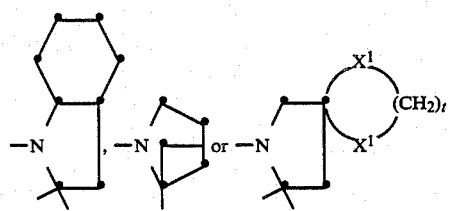

where t is 1-4 and X¹ is O or S;

(5) heterocycles having the formula

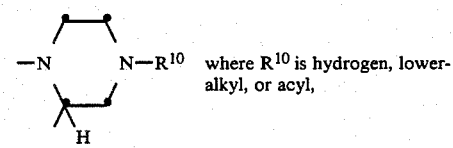 where R¹⁰ is hydrogen, loweralkyl, or acyl,

-continued

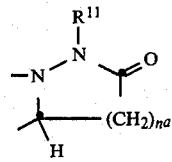 where R¹¹ is hydrogen, loweralkyl, aryl, substituted aryl, or arloweralkyl and $n_a$ = 1-3

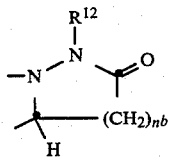 where R¹² is hydrogen, loweralkyl, aryl, substituted aryl, or arloweralkyl and $n_b$ = 1-3

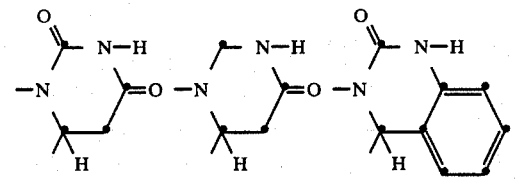

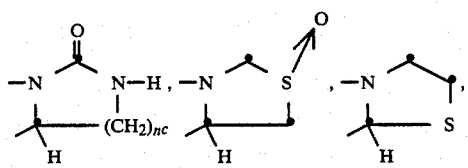

where $n_c$ = 1-2

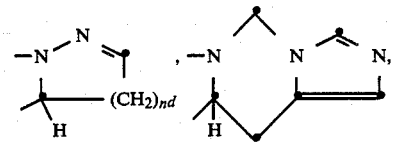

where $n_d$ = 1-3

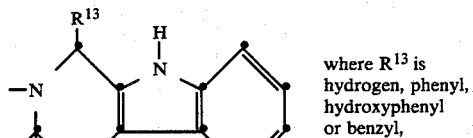 where R¹³ is hydrogen, phenyl, hydroxyphenyl or benzyl,

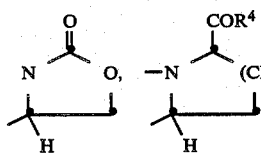 where $n_e$ = 1-2,

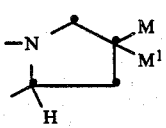 where M and M¹ are independently hydroxy, loweralkoxy, loweralkylthio, loweralkyl, or arloweralkyl, provided that M and M¹ may not both be hydroxy, 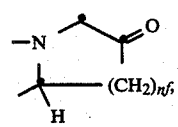 where $n_f$ = 1-3

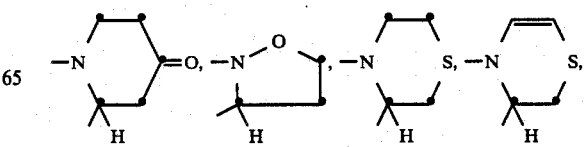

-continued

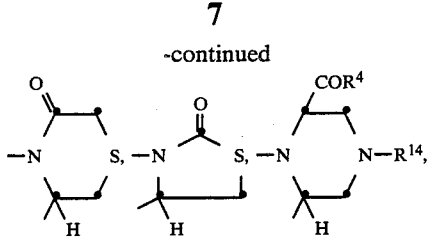

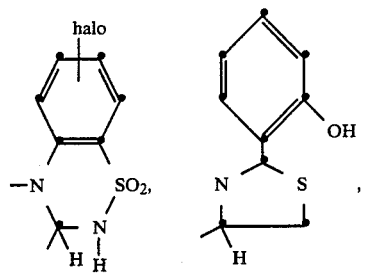

where $R^{14}$ is hydrogen, loweralkyl, arloweralkyl, or loweralkylcarbonyl;

$R^3$ is

where n is 1-3; and the $R^a$'s and $R^b$'s on each carbon are independently hydrogen; or loweralkyl; and $R^4$ is hydroxy; loweralkoxy; aralkoxy; or aryloxy, or mono- or disubstituted aryloxy wherein the substituents are chloro; and a pharmaceutically acceptable salt thereof.

The alkyl substituents recited above denote straight and branched chain hydrocarbons of $C_1$-$C_{12}$ such as methyl, hexyl, propyl, dodecyl isopentyl, isopropyl, nopentyl, etc.

Loweralkyl denotes alkyl groups of $C_1$ to $C_8$ such as ethyl, isobutyl, 4-methylpentyl, and the like.

Alkenyl and alkynyl denote alkyl groups as described above which are modified so that each contains a carbon to carbon double bond or triple bond, respectively, such as vinyl, 2-butenyl and 1-hexynyl.

Cycloalkyl denotes rings composed of 5 to 8 methylene groups, each which may be substituted or unsubstituted with other hydrocarbon substituents, and include, for example, cyclopentyl, cycloheptyl, 4-methyl cyclohexyl, and the like.

Benzofused cycloalkyl groups denote a cycloalkyl ring of 5 to 8 carbon atoms to which is fused a benzene ring such as indanyl or tetralyl groups.

Bicycloalkyl denotes two cycloalkyl rings of 5 to 8 carbon atoms each joined together in any allowable way such as perhydroindane, octahydronaphthalene, bicyclo 3:1:3 octane and spiro 4:0:4 nonane.

The loweralkoxy substituent represents a loweralkyl group as described above attached through an oxygen bridge.

The aralkyl and heteroaralkyl substituents recited above represent aryl or heteroaryl groups as herein defined attached through a straight or branched chain hydrocarbon of from one to six carbon atoms, for example, benzyl, phenethyl, 3,3-diphenylpropyl, 3-indolylmethyl, and the like.

Halo means chloro, bromo, iodo, or fluoro.

The aryl substituent represents phenyl, naphthyl, or biphenyl.

The heteroaryl substituent recited above represents any 5- or 6-membered aromatic ring containing from one to three heteroatoms selected from the group consisting of nitrogen, oxygen, and sulfur, for example, pyridyl, thienyl, furyl, imidazolyl, and thiazolyl; as well as any bicyclic group in which any of the above heterocyclic rings is fused to another aromatic ring, for example, indolyl, quinolinyl, isoquinolinyl, benzimidazolyl, benzothiazolyl, benzthienyl, and naphthyridyl.

The acylamino substituent represents loweralkanoylamino and aroylamino.

The Formula I compounds can be used in the form of salts derived from inorganic or organic acids and bases. Included among such acid addition salts are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfoate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Water or oil-soluble or dispersible products are thereby obtained.

In the compounds of Formula I, the carbon atoms to which $R^1$ and $R^2$ are attached, as well as the carbon atom of the $R^3$ substituent, may be asymmetric. These compounds accordingly exist in diastereo-isomeric forms or in mixtures thereof. Although the L- or S-configuration is preferred for each of the asymmetric carbon atoms, diastereomers containing D- or R- amino acids have activity dependent upon their structures and have advantages with respect to metabolic stability and can, therefore, be utilized in mixture or as pure diastereomeric compounds.

Preferred compounds of the present invention are those of Formula I wherein:

R is hydrogen or loweralkyl;

$R^1$ is alkyl of 1-10 carbon atoms which include branched, cyclic and unsaturated alkyl groups; substituted loweralkyl wherein the substituent can be hydroxy, lower alkylthio, amino, alkylamino, lowerdialkylamino, and acylamino; substituted loweralkyl having the formula $R_4{}^1(CH_2)_n$—Q—$(CH_2)_m$— wherein n is 0-2, m is 1-3, $R_4{}^1$ is aryl or heteroaryl optionally substituted by alkyl, halo, dihalo, amino, cyano, hydroxy, or alkoxy, and Q is O, S, N—$R_B{}^1$, $CONR_C{}^1$, $NR_C{}^1CO$, or CH=CH wherein $R_B{}^1$ is hydrogen, loweralkyl, aralkyl, loweralkanoyl, or aroyl and $R_C{}^1$ is hydrogen or loweralkyl; aralkyl or heteroaralkyl which include branched loweralkyl groups; substituted aralkyl or substituted heteroaralkyl which include branched loweralkyl groups wherein the loweralkyl substituents can be amino, acylamino, or hydroxy and the aryl and heteroaryl substituents can be loweralkyl, halo, dihalo, amino, cyano, hydroxy, loweralkoxy, aminoloweralkyl, or hydroxyloweralkyl.

$R^2$ is loweralkyl; aminoloweralkyl; phenylloweralkyl; or halophenylloweralkyl;

n is 1 or 2;

the $R^a$'s and $R^b$'s are hydrogen;

$R^4$ is hydroxy; loweralkoxy; and,

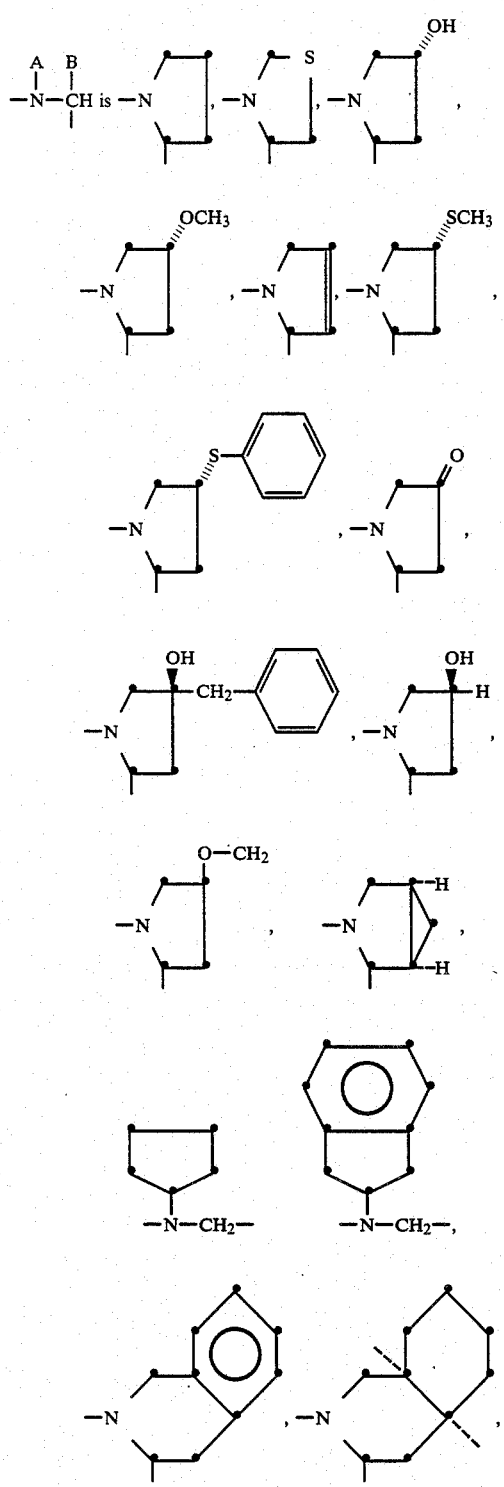

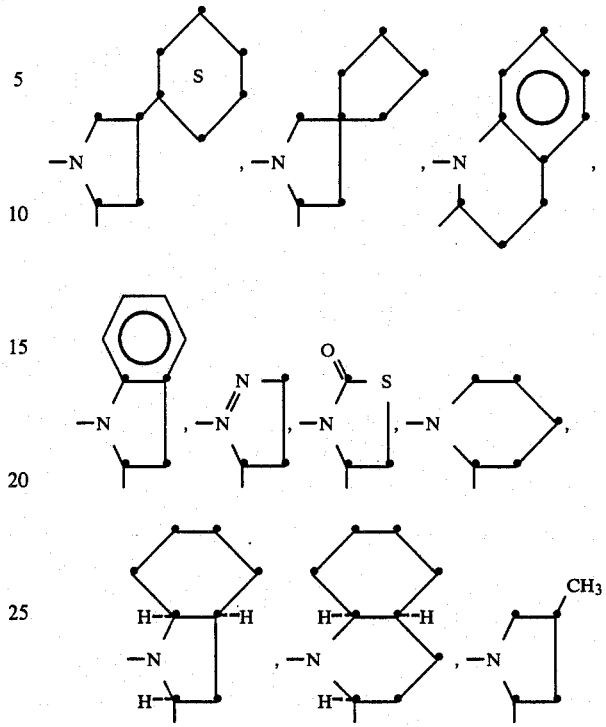

Especially preferred compounds of the present invention are the following:

N-[1-(S)-carboxy-3-phenylpropyl]-L-alanyl-(S)-2-pyrrolidineacetic acid, and ethyl ester;

N-[1-(S)-carboethoxy-3-phenylpropyl]-(S)-2-pyrrolidineacetic acid, and ethyl ester;

N-[1-(S)-carboxy-3-phenylpropyl]-L-lysyl-(S)-2-pyrrolidineacetic acid, and ethyl ester;

N-[1-(S)-carboethoxy-3-phenylpropyl]-L-alanyl-(S)-3-(2-pyrrolidine)propionic acid, and ethyl ester;

N-[1-(S)-carboxy-3-phenylpropyl]-L-lysyl-(S)-3-(2-pyrrolidine)propionic acid, and ethyl ester;

N-[1-(S)-carboethoxy-3-phenylpropyl]-L-alanyl-(S)-4-(2-pyrrolidine)butyric acid, and ethyl ester;

N-[1-(S)-carboxy-3-phenylpropyl]-L-lysyl-(S)-4-(2-pyrrolidine)butyric acid, and ethyl ester;

N-[1-(S)-carboethoxy-3-phenylpropyl]-L-alanyl-(S)-2-piperidineacetic acid, and ethyl ester;

N-[1-(S)-carboxy-3-phenylpropyl]-L-lysyl-(S)-4-(2-piperidine)butyric acid, and ethyl ester;

N-[1-(S)-carboxy-3-(4'-chlorophenyl)propyl]-L-alanyl-(S)-2-pyrrolidineacetic acid, and ethyl ester;

N-[1-(S)-carboethoxy-3-(4'-chlorophenyl)propyl]-L-alanyl-(S)-3-(2-pyrrolidine)propionic acid, and ethyl ester;

N-[1-(S)-carboxy-3-phenylpropyl]-L-lysyl-(S)-2-thiazolidineacetic acid, and ethyl ester;

N-[1-(S)-carboethoxy-3-phenylpropyl]-L-alanyl-(S)-4-(2-thiazolidine)butyric acid, and ethyl ester;

N-[1-(S)-carboxy-3-(4'-chlorophenyl)propyl]-L-lysyl-(S)-2-hexahydroindoleacetic acid, and ethyl ester;

N-[1-(S)-carbethoxy-3-phenylpropyl]-L-alanyl-(S)-2-(1,2,3,4-tetrahydroisoquinoline)acetic acid and ethyl ester;

N-[1-(S)-carboxy-3-phenylpropyl]-L-lysyl-(S)-2-(1,2,3,4-tetrahydroisoquinoline)acetic acid and ethyl ester;

N-[1-(S)-carbethoxy-3-phenylpropyl]-L-alanyl-(N-indanyl)-β alanine and ethyl ester; and, N-[1-(S)-carboxy-3-phenylpropyl]-L-lysyl-3-(2-indanylamino)propionic acid and ethyl ester.

The compounds of this invention inhibit angiotensin converting enzyme and thus block conversion of the decapeptide angiotensin I to angiotensin II. Angiotensin II is a potent pressor substance. Thus blood-pressure lowering can result from inhibition of its biosynthesis especially in animals and humans whose hypertension is angiotensin II related. Furthermore, converting enzyme degrades the vasodilator peptide, bradykinin. Therefore, inhibitors of angiotensin converting enzyme may lower blood-pressure also by potentiation of bradykinin. Although the relative importance of these and other possible mechanisms remains to be established, inhibitors of angiotensin converting enzyme are effective antihypertensive agents in a variety of animal models and are useful clinically, for example, in many human patients with renovascular, malignant and essential hypertension. See, for example, D. W. Cushman et al., *Biochemistry* 16, 5484 (1977).

The evaluation of converting enzyme inhibitors is guided by in vitro enzyme inhibition assays. For example, a useful method is that of Y. Piquilloud, A. Reinharz and M. Roth, *Biochem. Biophys. Acta*, 206, 136 (1970) in which the hydrolysis of carbobenzyloxyphenylalanylhistidinylleucine is measured. In vivo evaluations may be made, for example, in normotensive rats challenged with angiotensin I by the technique of J. R. Weeks and J. A. Jones, *Proc. Soc. Exp. Biol. Med.*, 104, 646 (1960) or in a high renin rat model such as that of S. Koletsky et al., *Proc. Soc. Exp. Biol. Med.*, 125, 96 (1967).

Thus, the compounds of the invention are useful in treating hypertension. They are also of value in the management of acute and chronic congestive heart failure, in the treatment of secondary hyperaldosteronism, primary and secondary pulmonary hypertension, renal failure and renal vascular hypertension, and in the management of vascular disorders such as migraine or Raynaud's disease. The application of the compounds of this invention for these and similar disorders will be apparent to those skilled in the art.

Thus, in accordance with the present invention there is provided a pharmaceutical composition for treating hypertension comprising a pharmaceutically acceptable carrier and an antihypertensively effective amount of a compound of Formula I.

There is also provided, in accordance with the present invention, a method of treating hypertension comprising administering to a patient in need of such treatment an antihypertensively effective amount of a compound of Formula I.

For the purpose of treating hypertension and those clinical conditions noted above, the compounds of the present invention may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, dogs, cats, etc., the compounds of the invention are effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide a pharmaceutically elegant and palatable preparation. Tablets contain the active ingredient in admixture with non-toxic pharmaceutically acceptable excipients which are suitable for manufacture of tablets. These excipients may be, for example, inert diluents, such as calcium carbonate, sodium carbonate, lactose, calcium phosphate or sodium phosphate; granulating and disintegrating agents, for example maize starch, or alginic acid; binding agents, for example, starch, gelatine or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate alone or with a wax may be employed.

Formulations for oral use may also be presented as hard gelatine capsules wherein the active ingredient is mixed with an inert solid diluent, for example, calcium carbonate, calcium phosphate or kaolin, or as soft gelatine capsules wherein the active ingredient is mixed with water or an oil medium, for example arachis oil, peanut oil, liquid paraffin or olive oil.

Aqueous suspensions contain the active materials in admixture with excipients suitable for the manufacture of aqueous suspensions. Such excipients are suspending agents, for example sodium carboxymethyl cellulose, methylcellulose, hydroxypropylmethylcellulose, sodium alginate, polyvinylpyrrolidone, gum tragacanth and gum acacia; dispersing or wetting agents may be a natural-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyoxyethylene sorbitan mono-oleate. The said aqueous suspensions may also contain one or more preservatives, for example, ethyl or n-propyl p-hyroxy benzoate, one or more coloring agents, one or more flavoring agents and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oil suspensions may contain a thickening agent, for example beeswax, hard paraffin or cetyl alcohol. Sweetening agents, such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oils, or a mineral oil, for example liquid paraffin or mixtures of these. Suitable emulsifying agents may be naturally-occurring gums, for example gum acacia or gum tragacanth, naturally-occurring phosphatides, for example soya bean lecithin, and esters or partial esters derived from fatty acids and hexitol anhydrides, for example sorbitan mono-oleate, and condensation products of the said partial esters with ethylene oxide, for example polyoxyethylene sorbitan mono-oleate. The emulsions may also contain sweetening and flavoring agents.

Syrups and elixirs may be formulated with sweetening agents, for example glycerol, sorbitol or sucrose. Such formulations may also contain a demulcent, a preservative and flavoring and coloring agents. The pharmaceutical compositions may be in the form of a sterile injectable preparation, for example as a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectibles.

The compounds of this invention may also be administered in the form of suppositories for rectal administration of the drug. These compositions can be prepared by mixing the drug with a suitable non-irritating excipient which is solid at ordinary temperatures by liquid at the rectal temperature and will thereofore melt in the rectum to release the drug. Such materials are cocoa butter and polyethylene glycols.

Dosage levels of the order of 10 to 1000 mg per patient per day, in single or multiple doses, are useful in the treatment of hypertension. Preferably, the dosage range will be from 20 to 500 mg per day.

The amount of active ingredient that may be combined with the carrier materials to produce a single dosage form will vary depending upon the host treated and the particular mode of administration.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

The compounds of this invention can also be administered in combination with other antihypertensives and/or diuretics. For example, the compounds of this invention can be given in combination with such compounds as acetazolamide, amiloride, aminophylline, atenolol, bendroflumethiazide, benzthiazide, bumetanide, chlorothalidone, chlorothiazide, clonidine, cryptenamine acetates and cryptenamine tannates, cyclothiazide, deserpidine, diazoxide, diltiazem, (S)-1-[[2-(3,4-dimethoxyphenyl)-ethyl]amino]-3-[[4-(2-thienyl)-1H-imidazol-2-yl]-phenoxy]-2-propanal, ethacrynic acid, flumethiazide, furosemide, guanethidene sulfate, hydralazine hydrochloride, hydrochlorothiazaide, hydroflumethiazide, (+)-4-[3-[-[2-(1-hydroxycyclohexyl)ethyl]-4-oxo-2-thiazolidinyl]propyl]-benzoic acid, indacrinone and variable ratios of its enantiomers, merethoxylline procaine, methylclothiazide, methyldopa, methyldopate hydrochloride, metolazone, metoprolol tartate, minoxidil, nadolol, nifedipine, pargyline hydrochloride, pindolol, polythiazide, prazosin, propranolol, quinethazone, rauwolfia serpentina, rescinnamine, reserpine, sodium ethacrynate, sodium nitroprusside, spironolactone, ticrynafen, timolol, triamterene, trichloromethiazide, trimethophan camsylate, verapamil, and the like, as well as admixtures and combinations thereof.

Typically, the individual daily dosages for these combinations can range from about one-fifth of the minimally recommended clinical dosages to the maximum recommended levels for the entities when they are given singly.

To illustrate these combinations, one of the antihypertensives of this invention effective in the 20 to 500 mg per day range can be effectively combined at levels at the 10 to 500 mg per day range with the following compounds at the indicated per day dose range: hydrochlorothiazide (10–100 mg); chlorothiazide (125–2000 mg); manipulated indacrinone enantiomer ratio (25–150 mg); ethacrynic acid (15–2000 mg); amiloride (5–20 mg); furosemide (5–80 mg); propranolol (20–480 mg); timolol (5–60 mg); and methyldopa (65–2000 mg); and the pivaloyloxyethyl ester of methyldopa (30–1000 mg). In addition, triple drug combinations of hydrochlorothiazide (10–100 mg) plus amiloride (5–20 mg) plus converting enzyme inhibitor of this invention (10–500 mg); hydrochlorothiazide (10–100 mg) plus timolol (5–60 mg) plus the converting enzyme inhibitor of this invention (10–500 mg); or manipulated indacrinone enantiomer ratio (25–150 mg) plus amiloride (5–20 mg) plus converting enzyme inhibitor of this invention (10–500 mg) are effective combinations to control blood pressure in hypertensive patients. Naturally, these dose ranges can be adjusted on a unit basis as necessary to permit divided daily dosage and, as noted above, the dose will vary depending on the nature and severity of the disease, weight of patient, special diets and other factors.

Typically, these combinations can be formulated into pharmaceutical compositions as discussed below.

About 10 to 500 mg of a compound or mixture of compounds of Formula I or a physiologicaly acceptable salt is compounded with a physiologically acceptable vehicle, carrier, excipient, binder, preservative, stablizer, flavor, etc., in a unit dosage form as called for by accepted pharmaceutical practice. The amount of active substance in these compositions or preparations is such that a suitable dosage in the range indicated is obtained.

The compounds of Formula I can be prepared by one or more of the methods described further below.

As will be evident to those skilled in the art and as demonstrated in the Examples which follow, reactive groups not involved in the reactions, such as amino, carboxy, mercapto, etc., may be protected by methods standard in peptide chemistry prior to the coupling reactions and subsequently deprotected to obtain the desired products.

METHOD OF PREPARATION (for Formula I, R=hydrogen or ethyl;
$R^1$=phenethyl; $R^2$=methyl; for $R^3$, $R^a$=$R^b$=hydrogen and n=1; and
$R^4$=hydroxy or ethoxy)

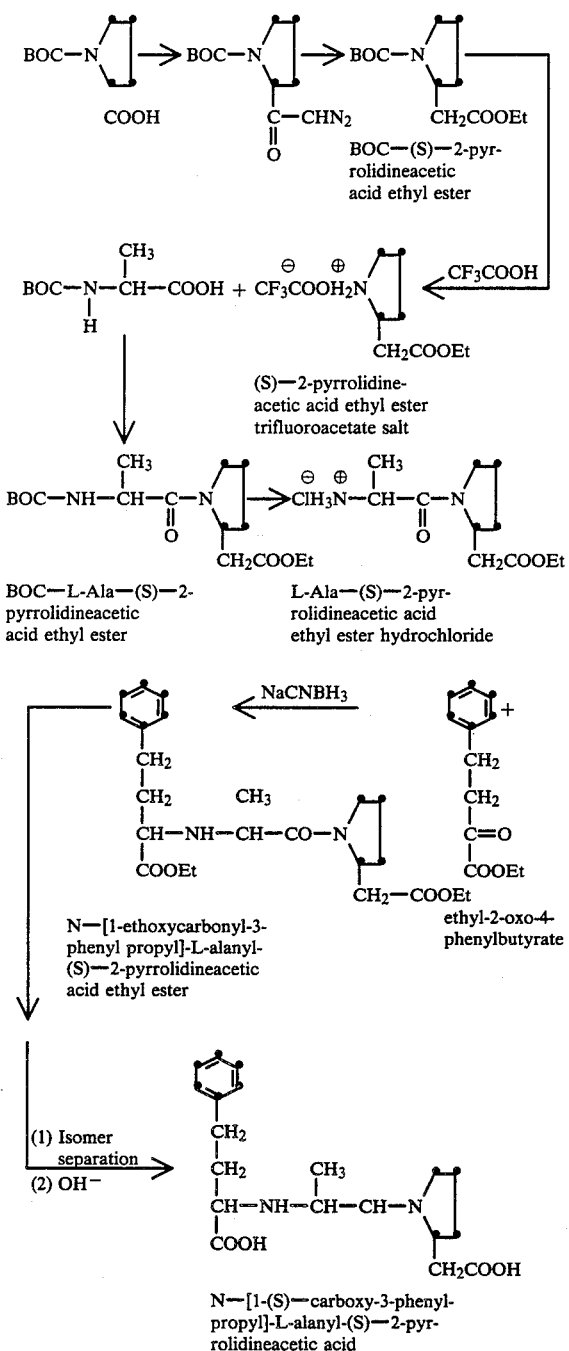

In the above preparation, the ethyl 2-oxo-4-phenylbutyrate may be represented by the general formula $R^1$—C=O, where R and $R^1$ are as

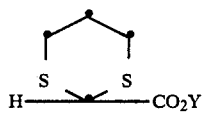  (II.)

previously defined. Thus, other α-keto acids or esters may be utilized to prepare other compounds of the present invention for various definitions of R and $R^1$. Such α-keto acids are readily available or may be prepared by well known techniques. For example, synthons such as

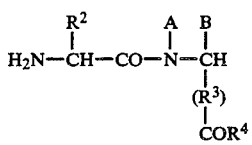

can be converted to α-keto acids or esters using methods involving alkylation followed by hydrolysis as described in the literature. An excellent method involves the reaction of Grignard reagents $R^1$MgX with ClCO-$CO_2Y$ or $YO_2CCO_2Y$. Another method involves condensing substituted acetic acid esters with diethyl oxalate followed by hydrolytic decarboxylation under acidic conditions to obtain α-keto acids. Carefully controlled acid hydrolysis in alcohol of acyl cyanides, which are prepared from acid chlorides and cuprous cyanide, also proves to be a viable synthetic route to α-keto esters. Nucleophilic displacement reactions on chloro or bromo pyruvic acid (ester) can also be used to produce a variety of interesting α-keto acids (esters). In these formulae, Y is a group such as loweralkyl or benzyl and protecting groups are employed as necessary in the $R^1$ group if an interfering functionality is present.

The α-keto acid or ester is condensed with a dipeptide of the formula:

$$H_2N-\underset{\underset{}{R^2}}{CH}-CO-\underset{\underset{}{(R^3)}}{\underset{}{N}}-\underset{\underset{}{COR^4}}{\overset{\overset{A}{|}}{C}}\overset{B}{H}$$ (III.)

which may be employed as the quaternary salt form, and which in the particular preparation illustrated in the flow sheet above, is L-Ala-L-2-pyrrolidineacetic acid ethyl ester hydrochloride. The condensation is preferably carried out in aqueous solution, optimally near neutrality, or mixed with or in a suitable organic solvent, such as ethanol or tetrahydrofuran, in the presence of sodium cyanoborohydride.

In turn, the dipeptide of Formula III may be prepared in accordance with techniques well known in peptide synthesis, involving, for example, reactive group protection during the coupling reaction with blocking groups such as N-formyl, N-t-butoxycarbonyl, and N-carbobenzyloxy, followed by their removal. Removable ester groups such as benzyl, ethyl, t-butyl, and N-hydroxysuccinamide may also be employed. Condensing agents in this preparation are typically those useful in peptide chemistry such as dicyclohexylcarbodiimide (DCC) or diphenylphosphoryl azide (DPPA).

The synthetic route described above may be shown in more general terms as follows:

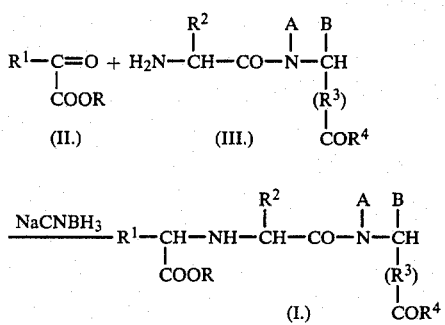
$$\xrightarrow{NaCNBH_3}$$
Additional compounds of Formula I can be prepared by employing the keto acids and keto esters listed in Table I below.
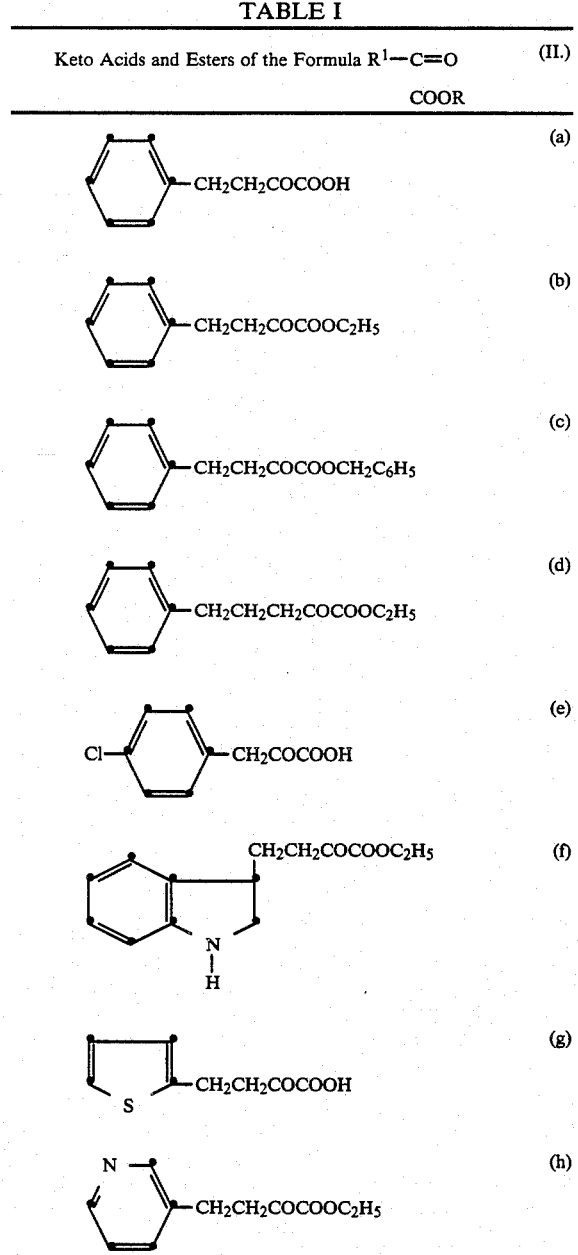
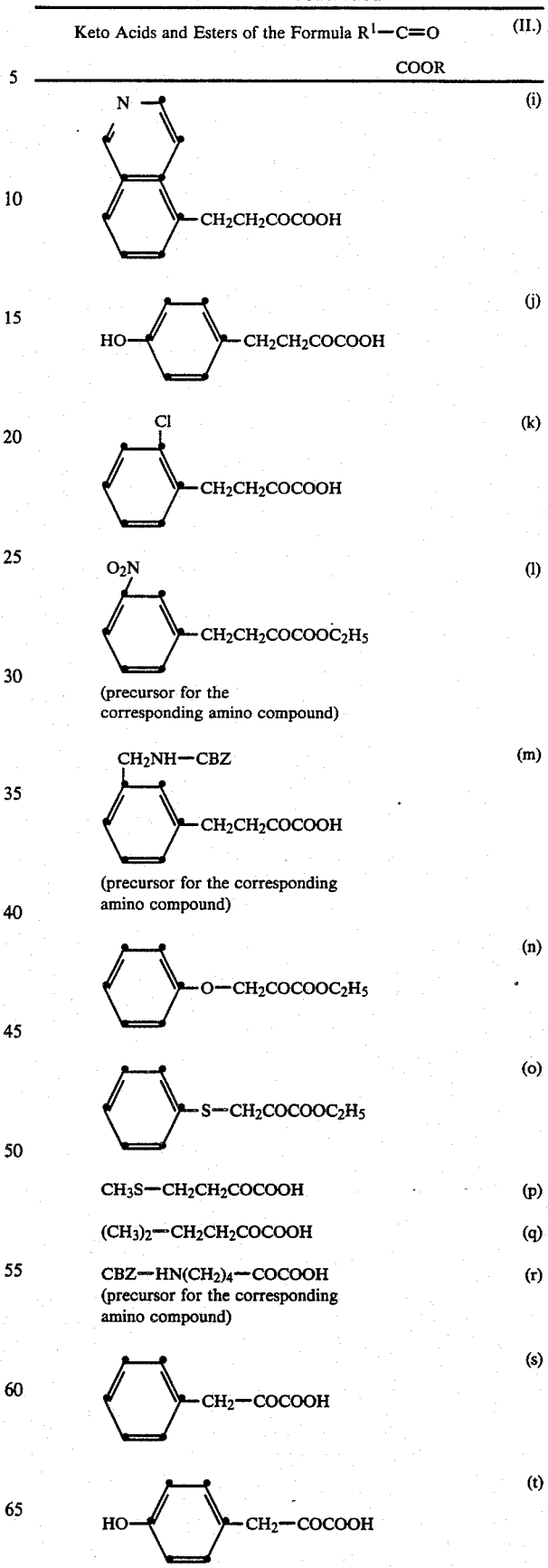

TABLE I-continued

Keto Acids and Esters of the Formula $R^1$—C=O (II.)
$$\text{COOR}$$

(u) [indole structure with $CH_2$—COCOOH substituent]

As already described above, the dipeptide of Formula III is prepared by conventional means. This synthesis may be illustrated by the following equation in which "B" represents a conventional blocking group and "E" represents hydrogen or an activated ester group.

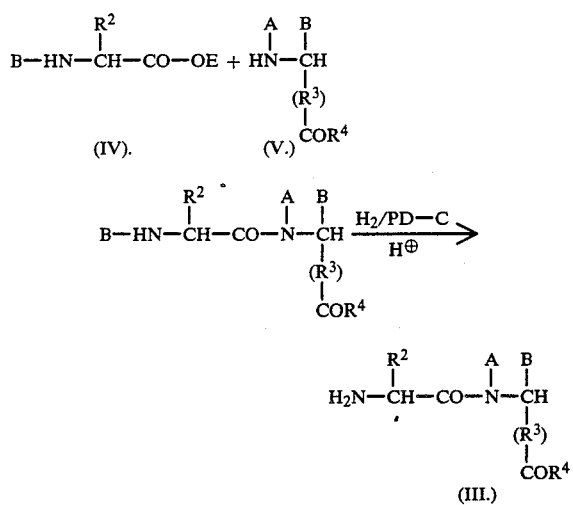

(III.)

Suitable amino acid starting materials of Formulas IV and V are shown in Table II below:

TABLE II

Amino Acid Starting Materials of the Formulas:

$$\underset{(IV.)}{B-HN-\underset{\underset{R^2}{|}}{CH}-CO-OE} \quad \underset{(V.)}{\underset{\underset{COR^4}{|}}{\underset{(R^3)}{|}}{HN-\underset{\underset{}{|}}{CH}}{\underset{B}{|}}^A}$$

| (IV.) | | (V.) |
|---|---|---|
| CBZ—L-Phe—OSu | | (S)—2-pyrrolidineacetic acid ethyl ester |
| CBZ—pCl—L-Phe | CBZ—L-Trp | |
| CBZ—L-Leu | CBZ—L-Cys | (S)—2-pyrrolidineacetic acid methyl ester |
| CBZ—L-Ala | CBZ—L-Met | |
| CBZ—L-Gly | CBZ—L-Tyr | (S)—3-(2-pyrrolidine)propionic acid benzyl ester |
| CBZ—L-Val | | |
| CBZ—L-Ile | | (S)—4-(2-pyrrolidine)butyric acid ethyl ester |
| CBZ—L-Ser | | |
| CBZ—L-Thr | | (S)—4-(2-piperidine)butyric acid ethyl ester |
| CBZ—L-Orn | | |
| BOC—L-Ala | | (S)—2-(3,4-methanopyrrolidine)acetic acid ethyl ester |
| Nα-CBZ, N—BOC—L-Lys | | |
| Nα-CBZ, N—BOC—L-Orn | | (S)—2-indoleacetic acid ethyl ester |
| | | (S)—2-hexahydroindoleacetic acid ethyl ester |
| | | (S)—2-(4,4-ethylenethiopyrrolidine)acetic acid methyl ester |
| | | (S)—2-thiazolidineacetic acid ethyl ester |

TABLE II-continued

Amino Acid Starting Materials of the Formulas:

$$\underset{(IV.)}{B-HN-\underset{\underset{R^2}{|}}{CH}-CO-OE} \quad \underset{(V.)}{\underset{\underset{COR^4}{|}}{\underset{(R^3)}{|}}{HN-\underset{\underset{}{|}}{CH}}{\underset{B}{|}}^A}$$

(S)—2-(1,2,3,4-tetrahydroisoquinoline)acetic acid ethyl ester
(S)—3-(2-indoline)propionic acid ethyl ester
N—(2-indanylamino)-β-alanine ethyl ester The amino acid starting materials of Formula V are either commercially available, or may be prepared by the procedure of Ondetti and Engel, *J. Med. Chem.*, 18, 761 (1975), by going through the intermediate diazoketone. This preparation may be illustrated as follows:

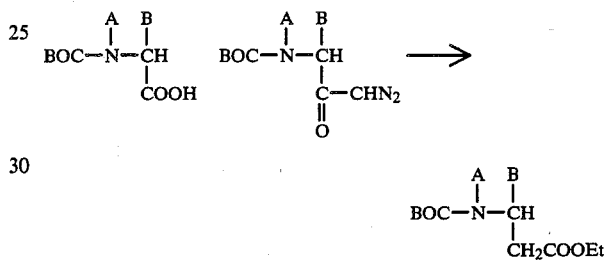

For example, BOC-(S)-2-pyrrolidineacetic acid is prepared from the corresponding ethyl ester (Example 1, Step A below) by the saponification procedure of Example 2 below, and is converted into BOC-(S)-3-(2-pyrrolidine)propionic acid ethyl ester by the procedure of Example 1, Step A. Then, by the procedures detailed in the Examples below, this compound is converted into N-[1-(S)-carboxy-3-phenylpropyl]-L-alanyl-(S)-3-(2-pyrrolidine)propionic acid and ethyl ester. In a similar manner, the butyric acid homolog may be prepared. If required by interference from functional groups in the starting materials, protection-deprotection steps may be interpolated into the synthetic sequence.

The following examples further illustrate preparation of the compounds of the present invention, but are not intended to in any way limit the scope thereof.

EXAMPLE 1

N-[1-(S)-Carboethoxy-3-phenylpropyl]-L-alanyl-(S)-2-pyrrolidineacetic acid ethyl ester Step A: t-Butoxycarbonyl-(S)-2-pyrrolidineacetic acid ethyl ester N-t-Butoxycarbonyl-L-proline (5.4 g; 25 mmol) was converted into the corresponding diazoketone by the procedure of M. A. Ondetti and S. L. Engel [*J. Med. Chem.* 18, 761, (1975)]. The diazoketone (4.9 g, 20.5 mmol) was stirred at room temperature in 30 ml of ethanol. Silver benzoate (ca. 30 mg) in 0.3 ml triethylamine was added and nitrogen evolution began. After 2 hours, the mixture was treated with charcoal, filtered, the precipitate washed with ethanol and the combined filtrate and washings concentrated to dryness. The residue was taken up in ethyl acetate and the latter solution washed with dilute HCl, dilute NaHCO$_3$, saturated aqueous NaCl, dried over Na$_2$SO$_4$ and concentrated to dryness. The residue was chromatographed on silica gel eluting with 2.5:1-hexane:ethyl acetate to give 3.497 g of the desired BOC-(S)-2-pyrrolidineacetic acid ethyl ester; ms M+ 25.7, 184; TLC R$_f$ 0.55, silica gel 2.5:1-hexane:ethyl acetate; NMR and IR in accord with structure.

Step B: (S)-2-Pyrrolidineacetic acid ethyl ester trifluoroacetate salt

To a stirred solution of BOC-(S)-2-pyrrolidineacetic acid ethyl ester (3.34 g; 13 mmol) in 10 ml methylene chloride at 0° C. was added 20 ml of trifluoroacetic acid. The mixture was stirred 0.5 hours at 20° C. and concentrated to dryness. Addition of ether (20 ml) yielded the crystalline trifluoroacetate salt which was recrystallized from ether-hexane; m.p. 64°–66° C.; NMR in accord with structure.

Step C: BOC-L-Alanyl-(S)-2-pyrrolidineacetic acid ethyl ester

To a stirred solution at 0° C. of (S)-2-pyrrolidineacetic acid ethyl ester trifluoroacetate salt (1.07 g; 3.95 mmol) and triethylamine (4.04 mg; 4.00 mmol) in 12 ml methylene chloride was added BOC-L-alanine (755 mg; 4.00 mmol), followed by hydroxybenztriazole (670 mg; 4.00 mmol) and dicyclohexylcarbodiimide (840 mg; 4.1 mmol). The mixture was kept 2 hours at 0° C. and 18 hours at room temperature. The mixture was then filtered, the precipitate washed with methylene chloride and the combined filtrate and washings washed with dilute HCl, dilute NaHCO$_3$, saturated aqueous NaCl solution, dried over Na$_2$SO$_4$ and concentrated to give the product dipeptide as a single component viscous oil 1.125 g (87%); TLC R$_f$=0.45 silica gel 1.5:1-ethyl acetate:hexane; NMR and IR in accord with structure.

Step D: L-Alanyl-(S)-2-pyrrolidineacetic acid ethyl ester hydrochloride

To the product of Step C above (1.125 g) in 3 ml of ethyl acetate at 0° C. was added 6 ml of 5.8M hydrogen-chloride in ethyl acetate, an the mixture was kept at 0° C. for 45 minutes. It was then concentrated to dryness; ether (20 ml) was added, and the crystalline hydrochloride salt was collected by filtration and washed with ether: 715 mg (80%) m.p. 175°–8° C.; TLC R$_f$=0.47 silica gel 4:1:1-n-butanol:water:acetic acid.

Step E: N-1-(S)-carbethoxy-3-phenylpropyl)-L-alanyl-(S)-2-pyrrolidineacetic acid ethyl ester A solution of L-alanyl-(S)-2-pyrrolidineacetic acid ethyl ester hydrochloride (610 mg; 2.34 mmol) in 3 ml of ethanol was neutralized with 2.5N NaOH and concentrated to dryness under reduced pressure. Anhydrous ethanol (5 ml) was added, followed by 2-oxo-4-phenylbutyric acid ethyl ester (1.00 g) and 1 g of ground 4A molecular sieves. The mixture was stirred for 30 minutes and sodium cyanoborohydride (310 mg) was added in portions over 2 hours. The mixture was stirred overnight, filtered and the filtrate taken to dryness. Ethanol (10 ml) and 2N hydrochloric acid (10 ml) were added and the mixture kept at room temperature 1 hour to destroy excess borohydride. Ethanol was removed under vacuum, water was added, and neutral α-keto ester was removed by ether extraction. The aqueous phase was made basic with solid Na$_2$CO$_3$ and extracted with ethyl acetate. The latter extract was washed with saturated aqueous NaCl solution, dried over Na$_2$SO$_4$, and concentrated to dryness to give the desired product as a 1:1 two component mixture; TLC R$_f$=0.34 and 0.43 silica gel 3:1-ethyl acetate-hexane. Chromatography on silica gel eluting with 3:1 ethyl acetate-hexane gave each pure diester. S,S,S-ms M+ 418; TLC R$_f$=0.34; NMR in accord with structure; $\alpha_D^{CHf}$ −49° (C=3.2); R,S,S-ms M+ 418; TLC R$_f$=0.43; NMR in accord with structure; $\alpha_D^{CHf}$ −45° (C=2.9).

EXAMPLE 2

N-[1-(S)-Carboxy-3-phenylpropyl]-L-alanyl-(S)-2-pyrrolidineacetic acid

A solution of N-(1-(S)-ethoxycarbonyl-3-phenylpropyl)-L-alanyl-(S)-2-pyrrolidineacetic acid ethyl ester (87 mg; 0.21 mmol) in 1 ml of ethanol and 1 ml of 1.0N sodium hydroxide was stirred overnight at room temperature. The mixture was concentrated under reduced pressure to remove ethanol, neutralized with dilute hydrochloric acid and poured onto a 80×12 mm column of Dowex 50W×4 ion exchange resin (H+ cycle). The column was eluted with 200 ml water followed by 100 ml of 2.5% pyridine in water. Evaporation under reduced pressure of the aqueous pyridine eluate gave the product desired as a white crystalline solid (72 mg) ms M+ 362; TLC R$_f$ 0.57-silica gel 4:1:1-n-butanol:water:acetic acid;

elemental analysis: calculated for: C$_{19}$H$_{26}$N$_2$O$_5$.H$_2$O; C, 59.98; H, 7.42; N, 7.36; Found: C, 60.35; H, 7.50; N, 7.37.

EXAMPLE 3

N-[1-(S)-Carboethoxy-3-phenylpropyl]-L-alanyl-(S)-2-pyrrolidineacetic acid

Step A: L-Alanyl-2-pyrrolidineacetic acid

L-Alanyl-(S)-2-pyrrolidineacetic acid ethyl ester hydrochloride is deprotected by treatment with boron tribromide in methylene chloride utilizing the procedure of A. M. Felix, *J. Org. Chem.*, 39, 1427 (1974).

Alternatively BOC-L-alanyl-(S)-2-pyrrolidineacetic acid ethyl ester is converted into BOC-L-alanyl-(S)-2-pyrrolidineacetic acid by treatment with sodium hydroxide in aqueous ethanol as described in Example 2. The alkaline reaction mixture is washed once with ether, acidified to pH 2 with dilute hydrochloric acid, extracted with ethyl acetate and the latter extract dried over sodium sulfate and concentrated to dryness under reduced pressure to give BOC-L-alanyl-(S)-2-pyrrolidineacetic acid. The BOC group is removed in hydrogen chloride-ethyl acetate as described in Example 1, Step D, to give L-alanyl-(S)-2-pyrrolidine acetic acid hydrochloride salt.

Step B: N-[1-(S)-Carboethoxy-3-phenylpropyl]-L-alanyl-(S)-2-pyrrolidineacetic acid To a solution of L-alanyl-(S)-2-pyrrolidineacetic acid (390 mg; 2.0 mmol) (from the hydrochloride neutralized with 2.5N NaOH) and ethyl 2-oxo-4-phenylbutyrate (1.00 g) in 5 ml of ethanol is added 1 g of ground 4A molecular sieves. The mixture is stirred for 30 minutes and sodium cyanoborohydride (310 mg) is added in portions over 2 hours. The mixture is stirred overnight, filtered, and the filtrate concentrated under reduced pressure to near dryness. The mixture is taken up in methylene chloride and washed with water. The methylene chloride layer is extracted with 5% aqueous potassium bicarbonate, the latter extract is acidified to pH 2 and extracted with methylene chloride. The organic extract is dried over sodium sulfate and concentrated to dryness under reduced pressure to give the desired product. The S,S,S and R,S,S diastereomers are separated using reverse phase HPLC.

EXAMPLE 4

N-[1-(R,S)-Carboxy-3-phenylpropyl]-L-lysyl-(S)-2-pyrrolidineacetic acid

Step A: N- -BOC-L-lysyl-(S)-2-pyrrolidineacetic acid ethyl ester

N-α-CBZ, N- -BOC-L-lysine and ethyl-2-pyrrolidineacetate are condensed by the procedure of Example 1, Step C to give N-α-CBZ, N- -BOC-L-lysyl-(S)-2-pyrrolidine acetic acid ethyl ester. The N-α-CBZ group is removed by hydrogenolysis in ethanol containing one equivalent of acetic acid over 10% palladium on charcoal utilizing the procedure of P. G. Katsoyannis and G. P. Schwartz, *Methods in Enzymology*, 47, 546 (1974), to give N- -BOC-L-lysyl-(S)-2-pyrrolidineacetic acid ethyl ester.

Step B: N-[1-(R,S)-carboxy-3-phenylpropyl]-L-lysyl-(S)-2-pyrrolidineacetic acid

The product of Step A above is condensed with 2-oxo-4-phenylbutyric acid ethyl ester by the procedure of Example 1, Step E. The diastereomers are separated by silica gel chromatography. The individual diastereomers are converted into the corresponding diacids by saponification as in Example 2 and the -BOC group is removed in hydrogen chloride in ethyl acetate by the procedure of Example 1, Step D. The resulting hydrochloride salt is converted to the free base by absorbing on a strong acid ion exchange resin (Dowex 50W; H+ cycle) and eluting with 3% pyridine in water. Freeze drying affords the desired product, and the S,S,S and R,S,S, diastereomers are separated using reverse phase HPLC.

What is claimed is:

1. A compound of the formula:

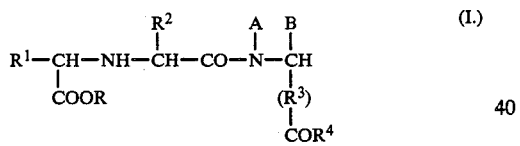

(I.)

wherein:

R is hydrogen, loweralkyl, aralkyl, aryl; or mono- or disubstituted aryl wherein the substituents are chloro;

$R^1$ is hydrogen; alkyl of from 1 to 12 carbon atoms which include branched, cyclic and unsaturated alkyl groups; substituted loweralkyl wherein the substituent can be halo, hydroxy, carboxy, carboxamido, loweralkylthio, loweralkoxy, loweralkoxycarbonyl, loweraralkoxycarbonyl, amino, loweralkylamino, lowerdialkylamino, loweralkanoylamino, aroylamino; substituted loweralkylamino wherein the substituent can be halo, hydroxy, alkoxy or cyano; arloweralkylamino; cyclic amino; oxo, thio or ureido; aryloxy; arylthio; aralkyloxy; aralkylthio; benzofused cycloalkyl or bicycloalkyl of from 8–12 carbon atoms; aryl or heteroaryl which may be mono-, di- or trisubstituted by loweralkyl, hydroxy, loweralkoxy, halo, amino, loweralkanoylamino, aroylamino, loweralkylthio or aminoloweralkyl; benzofused cycloalkyl or bicycloalkyl of from 8 to 12 carbon atoms; arloweralkyl; arloweralkenyl; heteroloweralkyl and heteroloweralkenyl in which the aryl or heteroaryl rings may be mono-, di- or trisubstituted by halo, loweralkyl, hydroxy, loweralkoxy, amino, loweralkylamino, diloweralkylamino, aminoloweralkyl, loweralkanoylamino, aroylamino, carboxy, haloloweralkyl, nitro, cyano or sulfonamido; aralkyl or heteroaralkyl which include branched loweralkyl groups; substituted aralkyl or substituted heteroaralkyl which include branched loweralkyl groups wherein the loweralkyl groups can be substututed by amino, loweralkanoylamino, aroylamino, or hydroxyl and the aryl and heteroaryl groups can be substituted by halo, dihalo, loweralkyl, hydroxy, loweralkoxy, aryloxy, aroyl, arylthio, amino, aminoloweralkyl, loweralkanoylamino, aroylamino, lowerdialkylamino, loweralkylamino, hydroxy, hydroxyloweralkyl, trihalololweralkyl, nitro, cyano, or sulfonamido; any of the arloweralkyl or alkenyl and heteroloweralkyl or alkenyl groups described above in which the aryl or heteroaryl ring is partially or completely hydrogenated; substituted loweralkyl having the formula $R_A{}^1(CH_2)_n$—Q—$(CH_2)_m$ wherein n is 0–2, m is 1–3, $R_A{}^1$ is aryl or heteroaryl optionally substituted by amino, lowerdialkylamino, loweralkylamino, hydroxy, hydroxyloweralkyl, aminoloweralkyl, trihalololweralkyl, cyano, nitro, sulfonamido, aroyl, loweralkyl, halo, dihalo, and loweralkoxy, and Q is O, S, SO, $SO_2$, N—$R_B{}^1$, $CONR_C{}^1$, $NR_C{}^1CO$, CH=CH wherein $R_B{}^1$ is hydrogen, loweralkyl, aryl, aralkyl, loweralkanoyl, or aroyl, and $R_C{}^1$ is hydrogen, or loweralkyl;

$R^2$ is hydrogen; loweralkyl; hydroxyloweralkyl; loweralkanoylamino; aminoloweralkyl, dimethylaminoloweralkyl; haloloweralkyl; guanidinoloweralkyl; mercaptoloweralkyl; loweralkylthioloweralkyl; aralkyl, heteroaralkyl, substituted aralkyl, or substituted heteroaralkyl, where the alkyl portion is loweralkyl and the substituents are halo, dihalo, loweralkyl, hydroxy, loweralkoxy, aryloxy, aroyl, arylthio, amino, aminoloweralkyl, loweralkanoylamino, aroylamino, lowerdialkylamino, loweralkylamino, hydroxyloweralkyl, trihalololweralkyl, nitro, cyano, or sulfonamido; mercaptoloweralkyl; or loweralkylthioloweralkyl; in the group:

A and B are joined, together with the nitrogen and carbon atoms to which they are attached to form a pyrrole ring having the formula:

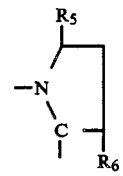

wherein $R^5$ is hydrogen, lower alkyl, aralkyl, or aryl, $R_6$ is hydrogen; loweralkyl; cycloalkyl; aryl; aralkyl; heteroaryl; loweralkyloxy; loweralkylthio; aryloxy; arylthio; arloweralkyloxy; arloweralkylthio; hydroxy; loweralkanoyloxy; loweralkanoyl; halo; amino; loweralkylamino; arloweralkylamino; heteroloweralkylamino; acylamino in which the acyl group may be loweralkanoyl, aroyl, heteroaroyl or heteroloweralkanoyl; carbamoyl or N-substituted carbamoyloxy; including any of these groups containing an aromatic ring wherein said ring may be mono-, di- or trisubstituted by loweralkyl, loweralkoxy, loweralkylthio, halo, hydroxy, aryl, aryloxy, arylthio or aralkyl; $R^3$ is

where n is 1–3; and the $R^a$'s and $R^b$'s on each carbon are independently hydrogen; or loweralkyl; and $R^4$ is hydroxy; loweralkoxy; aralkoxy; or aryloxy, or mono- or disubstituted aryloxy wherein the substituents are chloro; and a pharmaceutically acceptable salt thereof wherein in said $R-R^6$ groups the aralkyl and heteroaralkyl substituents represent aryl or heteroaryl groups attached through a straight or branched chain hydrocarbon of from one to six carbon atoms, selected from the group consisting of benzyl, phenethyl, 3,3-diphenylpropyl, 3-indolylmethyl; aryl represents phenyl, naphthyl, or biphenyl; and, heteroaryl represents any 5- or 6-membered aromatic ring containing from one to three nitrogen, oxygen and sulfur heteroatoms and is selected from the group consisting of pyridyl, thienyl, furyl, imidazolyl, and thiazolyl, as well as any bicyclic group in which any of the above heterocyclic rings is fused to another aromatic ring, and which is selected from the group consisting of indolyl, quinolinyl, isoquinolinyl, benzimidazolyl, benzothiazolyl, benzthienyl, and napthyridyl.

2. A pharmaceutical composition useful in the treatment of hypertension which comprises a pharmaceutically acceptable carrier; an antihypertensively effective amount of a compound of claim 1; and, an antihypertensively effective amount of an antihypertensive and/or diuretic compound selected from the group consisting of acetazolamide, amiloride, aminophylline, atenolol, bendroflumethiazide, benzthiazide, bumetanide, chlorothalidone, chlorothiazide, clonidine, cryptenamine acetates and cryptenamine tannates, cyclothiazide, deserpidine, diazoxide, diltiazem, (S)-1-[[2-(3,4-dimethoxyphenyl)ethyl]amino]-3-[[4-(2-thienyl)-1H-imidazol-2-yl]phenoxy]-2-propanol, ethacrynic acid, flumethiazide, furosemide, guanethidene sulfate, hydralazine hydrochloride, hydrochlorothiazaide, hydroflumethiazide, (+)-4-[3-[-[2-(1-hydroxycyclohexyl)ethyl]4-oxo-2-thiazolidinyl]propyl]-benzoic acid, indacrinone and variable ratios of its enantiomers, merethoxylline procaine, methylclothiazide, methyldopa, methyldopate hydrochloride, metolazone, metoprolol tartate, minoxidil, naldolol, nifedipine, pargyline hydrochloride, pindolol, polythiazide, prazosin, propranolol, quinethazone, rauwolfia serpentia, rescinnamine, reserpine, sodium ethacrynate, sodium nitroprusside, spironolactone, ticrynafen, timolol, triamterene, trichlormethiazide, trimethophan camsylate, and verapamil.

3. A pharmaceutical composition useful in the treatment of hypertension which comprises a pharmaceutically acceptable carrier; an antihypertensively effective amount of a compound of claim 1; and an antihypertensively effective amount of hydrochlorothiazide.

4. A pharmaceutical composition useful in the treatment of hypertension which comprises a pharmaceutically acceptable carrier; an antihypertensively effective amount of a compound of claim 1, and an antihypertensively effective amount of timolol.

5. A pharmaceutical composition useful in the treatment of hypertension which comprises a pharmaceutically acceptable carrier; an antihypertensively effective amount of a compound of claim 1; and an antihypertensively effective amount of manipulated indacrinone enantiomer ratio.

6. A pharmaceutical composition useful in treating hypertension comprising a pharmaceutically acceptable carrier and an antihypertensively effective amount of a compound of the formula:

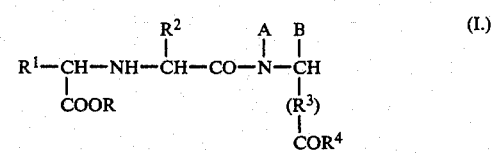

wherein:

R is hydrogen; loweralkyl; aralkyl, aryl; or mono- or disubstituted aryl wherein the substituents are chloro;

$R^1$ is hydrogen; alkyl of from 1 to 12 carbon atoms which include branched, cyclic and unsaturated alkyl groups; substituted loweralkyl wherein the substituent can be halo, hydroxy, carboxy, carboxamido, loweralkylthio, loweralkoxy, loweralkoxycarbonyl, loweraralkoxycarbonyl, amino, loweralkylamino, lowerdialkylamino, loweralkanoylamino, aroylamino; substituted loweralkylamino wherein the substituent can be halo, hydroxy, alkoxy or cyano; arloweralkylamino; cyclic amino; oxo, thio or ureido; aryloxy; arylthio; aralkyloxy; aralkylthio; benzofused cycloalkyl or bicycloalkyl of from 8–12 carbon atoms; aryl or heteroaryl which may be mono-, di- or trisubstituted by loweralkyl, hydroxy, loweralkoxy, halo, amino, loweralkanoylamino, aroylamino loweralkylthio or aminoloweralkyl; benzofused cycloalkyl or bicycloalkyl of from 8 to 12 carbon atoms; arloweralkyl; arloweralkenyl; heteroloweralkyl and heteroloweralkenyl in which the aryl or heteroaryl rings may be mono-, di- or tri-substituted by halo, loweralkyl, hydroxy, loweralkoxy, amino, loweralkylamino, diloweralkylamino, aminoloweralkyl, loweralkanoylamino, aroylamino, carboxy, haloloweralkyl, nitro, cyano or sulfonamido; aralkyl or heteroaralkyl which include branched loweralkyl groups; substituted aralkyl or substituted heteroaralkyl which include branched loweralkyl groups wherein the loweralkyl groups can be substituted by amino, loweralkanoylamino, aroylamino, or hydroxyl and the aryl and heteroaryl groups can be substituted by halo, dihalo, loweralkyl, hydroxy, loweralkoxy, aryloxy, aroyl, arylthio, amino, aminoloweralkyl, loweralkanoylamino, aroylamino, lowerdialkylamino, loweralkylamino, hydroxy, hydroxyloweralkyl, trihaloloweralkyl, nitro, cyano, or sulfonamido; any of the arloweralkyl or alkenyl and heteroloweralkyl or alkenyl groups described above in which the aryl or heteroaryl ring is partially or completely hydrogenated; substituted loweralkyl having the formula $R_A{}^1(CH_2)_n—Q—(CH_2)_m$ wherein n is 0–2, m is 1–3, $R_A{}^1$ is aryl or heteroaryl optionally substituted by amino, lowerdialkylamino, loweralkylamino, hydroxy, hydroxyloweralkyl, aminoloweralkyl, trihaloloweralkyl, cyano, nitro, sulfonamido, aroyl, loweralkyl, halo, dihalo, and loweralkoxy, and Q is O, S, SO, SO₂, N—$R_B^1$, CONR$_C^1$, NR$_C^1$CO, CH=CH wherein $R_B^1$ is hydrogen, loweralkyl, aryl, aralkyl, loweralkanoyl, or aroyl, and $R_C^1$ is hydrogen, or loweralkyl;

R² is hydrogen; loweralkyl; hydroxyloweralkyl; loweralkanoylamino; aminoloweralkyl; dimethylaminoloweralkyl; haloloweralkyl; guanidinoloweralkyl; mercaptoloweralkyl; loweralkylthioloweralkyl; aralkyl, heteroalkyl, substituted aralkyl, or substituted heteroaralkyl, where the alkyl portion is loweralkyl and the substituents are halo, dihalo, loweralkyl, hydroxy, loweralkoxy, aryloxy, aroyl, arylthio, amino, aminoloweralkyl, loweralkanoylamino, aroylamino, lowerdialkylamino, loweralkylamino, hydroxyloweralkyl, trihaloloweralkyl, nitro, cyano, or sulfonamido; mercaptoloweralkyl; or loweralkylthioloweralkyl; in the group;

A and B are joined, together with the nitrogen and carbon atoms to which they are attached to form a pyrrole ring having the formula:

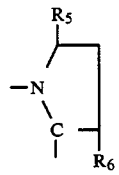

wherein R₅ is hydrogen, lower alkyl, aralkyl, or aryl; R₆ is hydrogen; loweralkyl; cycloalkyl; aryl; aralkyl; heteroaryl; loweralkyloxy; loweralkylthio; aryloxy; arylthio; arloweralkyloxy; arloweralkylthio; hydroxy; loeralkanoyloxy; loweralkanoyl; halo; amino; loweralkylamino; arloweralkylamino; heteroloweralkylamino; acylamino in which the acyl group may be loweralkanoyl, aroyl, heteroaroyl or heteroloweralkanoyl; carbamoyl or N-substituted carbamoyloxy; including any of these groups containing an aromatic ring wherein said ring may be mono-, di- or trisubstituted by loweralkyl, loweralkoxy, loweralkylthio, halo, hydroxy, aryl, aryloxy, arylthio or aralkyl;

R³ is

where
n is 1-3; and the R$^a$'s and R$^b$'s on each carbon are independently hydrogen; or loweralkyl; and
R⁴ is hydroxy; loweralkoxy; aralkoxy; or aryloxy, or mono- or disubstituted aryloxy wherein the substituents are chloro; and
a pharmaceutically acceptable salt thereof wherein in said R-R⁶ groups the aralkyl and heteroalkyl substituents represent aryl or heteroaryl groups attached through a straight or branched chain hydrocarbon of from one to six carbon atoms selected from the group consisting of benzyl, phenethyl, 3,3-diphenylpropyl, 3-indolylmethyl; aryl represents phenyl, naphthyl, or biphenyl; and, heteroaryl represents any 5-or 6-membered aromatic ring containing from one to three nitrogen, oxygen and sulfur heteroatoms and is selected from the group consisting of pyridyl, thienyl, furyl, imidazolyl, and thiazolyl, as well as any bicyclic group in which any of the above heterocyclic rings is fused to another aromatic ring, and which is selected from the group consisting of indolyl, quinolinyl, isoquinolinyl, benzimidazolyl, benzothiazolyl, benzthienyl, and naphthyridyl.

7. A method of treating hypertension comprising administering to a patient in need of such treatment an antihypertensively effective amount of a compound of the formula:

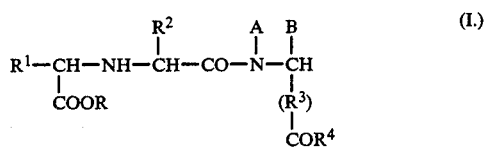

wherein:
R is hydrogen; loweralkyl; aralkyl; aryl; or mono- or disubstituted aryl wherein the substituents are chloro;

R¹ is hydrogen; alkyl of from 1 to 12 carbon atoms which include branched, cyclic and unsaturated alkyl groups; substituted loweralkyl wherein the substituent can be halo, hydroxy, carboxy, carboxamido, loweralkylthio, loweralkoxy, loweralkoxycarbonyl, loweraralkoxycarbonyl, amino, loweralkylamino, lowerdialkylamino, loweralkanoylamino, aroylamino; substituted loweralkylamino wherein the substituent can be halo, hydroxy, alkoxy or cyano; arloweralkylamino; cyclic amino; oxo, thio or ureido; aryloxy; arylthio; aralkyloxy; aralkylthio; benzofused cycloalkyl or bicycloalkyl of from 8-12 carbon atoms; aryl or heteroaryl which may be mono-, di- or trisubstituted by loweralkyl, hydroxy, loweralkoxy, halo, amino, loweralkanoylamino, aroylamino, loweralkylthio or aminoloweralkyl; benzofused cycloalkyl or bicycloalkyl of from 8 to 12 carbon atoms; arloweralkyl; arloweralkenyl; heteroloweralkyl and heteroloweralkenyl in which the aryl or heteroaryl rings may be mono-, di- or tri-substituted by halo, loweralkyl, hydroxy, loweralkoxy, amino, loweralkylamino, diloweralkylamino, aminoloweralkyl, loweralkanoylamino, aroylamino, carboxy, haloloweralkyl, nitro, cyano or sulfonamido; aralkyl or heteroaralkyl which include branched loweralkyl groups; substituted aralkyl or substituted heteroaralkyl which include branched loweralkyl groups wherein the loweralkyl groups can be substituted by amino, loweralkanoylamino, aroylamino, or hydroxyl and the aryl and heteroaryl groups can be substituted by halo, dihalo, loweralkyl, hydroxy, loweralkoxy, aryloxy, aroyl, arylthio, amino, aminoloweralkyl, loweralkanoylamino, aroylamino, lowerdialkylamino, loweralkylamino, hydroxy, hydroxyloweralkyl, trihaloloweralkyl, nitro, cyano, or sulfonamido; any of the arloweralkyl or alkenyl and heteroloweralkyl or alkenyl groups described above in which the aryl or heteroaryl ring is partially or completely hydrogenated; substituted loweralkyl having the formula $R_A{}^1(CH_2)_n$—Q—$(CH_2)_m$ wherein n is 0-2, m is 1-3, $R_A{}^1$ is aryl or heteroaryl optionally substituted by amino, lowerdialkylamino, loweralkylamino, hydroxy, hydroxyloweralkyl, aminoloweralkyl, trihaloloweralkyl, cyano, nitro, sulfonamido, aroyl, loweralkyl, halo, dihalo, and loweralkoxy, and Q is O, S, SO, $SO_2$, N—$R_B{}^1$, $CONR_C{}^1$, $NR_C{}^1CO$, CH=CH wherein $R_B{}^1$ is hydrogen, loweralkyl, aryl, aralkyl, loweralkanoyl, or aroyl, and $R_C{}^1$ is hydrogen, or loweralkyl;

$R^2$ is hydrogen; loweralkyl; hydroxyloweralkyl; loweralkanoylamino; aminoloweralkyl; dimethylaminoloweralkyl; haloloweralkyl; guanidinoloweralkyl; mercaptoloweralkyl; loweralkylthioloweralkyl; aralkyl, heteroaralkyl, substituted aralkyl, or substituted heteroaralkyl, where the alkyl portion is loweralkyl and the substituents are halo, dihalo, loweralkyl, hydroxy, loweralkoxy, aryloxy, aroyl, arylthio, amino, aminoloweralkyl, loweralkanoylamino, aroylamino, lowerdialkylamino, loweralkylamino, hydroxyloweralkyl, trihaloloweralkyl, nitro, cyano, or sulfonamido; mercaptoloweralkyl; or loweralkylthioloweralkyl; in the group:

A and B are joined, together with the nitrogen and carbon atoms to which they are attached to form a pyrrole ring having the formula:

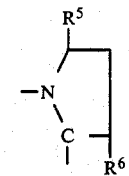

wherein $R_5$ is hydrogen, lower alkyl, aralkyl, or aryl; $R_6$ is hydrogen; loweralkyl; cycloalkyl; aryl; aralkyl; heteroaryl; loweralkyloxy; loweralkylthio; aryloxy; arylthio; arloweralkyloxy; arloweralkylthio; hydroxy; loweralkanoyloxy; loweralkanoyl; halo; amino; loweralkylamino; arloweralkylamino; heteroloweralkylamino; acylamino in which the acyl group may be loweralkanoyl, aroyl, heteroaroyl or heteroloweralkanoyl; carbamoyl or N-substituted carbamoyloxy; including any of these groups containing an aromatic ring wherein said ring may be mono-, di- or trisubstituted by loweralkyl, loweralkoxy, loweralkylthio, halo, hydroxy, aryl, aryloxy, arylthio or aralkyl;

$R^3$ is

n is 1-3; and the $R^a$'s and $R^b$'s on each carbon are independently hydrogen; or loweralkyl; and $R^4$ is hydroxy; loweralkoxy; aralkoxy; or aryloxy, or mono- or disubstituted aryloxy wherein the substituents are chloro; and a pharmaceutically acceptable salt thereof wherein in said R-$R^6$ groups the aralkyl and heteroaralkyl substituents represent aryl or heteroaryl groups attached through a straight or branched chain hydrocarbon of from one to six carbon atoms selected from the group consisting of benzyl, phenethyl, 3,3-diphenylpropyl, 3-indolylmethyl; aryl represents phenyl, naphthyl, or biphenyl; and, heteroaryl represents any 5- or 6-membered aromatic ring containing from one to three nitrogen, oxygen and sulfur heteroatoms and is selected from the group consisting of pyridyl, thienyl, furyl, imidazolyl, and thiazolyl, as well as any bicyclic group in which any of the above heterocyclic rings is fused to another aromatic ring, and which is selected from the group consisting of indolyl, quinolinyl, isoquionolinyl, benzimidazolyl, benzothiazolyl, benzthienyl, and naphthyridyl.

* * * * *